(12) United States Patent
Ishihara et al.

(10) Patent No.: US 9,162,972 B2
(45) Date of Patent: Oct. 20, 2015

(54) METHOD FOR PRODUCTION OF HYDROXYCARBOXYLIC ACID AMIDE COMPOUNDS AND NOVEL ARYLBORONIC ACID COMPOUND

(71) Applicant: NATIONAL UNIVERSITY CORPORATION NAGOYA UNIVERSITY, Nagoya-shi, Aichi (JP)

(72) Inventors: Kazuaki Ishihara, Nagoya (JP); Akira Sakakura, Nagoya (JP)

(73) Assignee: NATIONAL UNIVERSITY CORPORATION NAGOYA UNIVERSITY, Nagoya (JP)

(*) Notice: Subject to any disclaimer, the term of this patent is extended or adjusted under 35 U.S.C. 154(b) by 0 days.

(21) Appl. No.: 14/377,972

(22) PCT Filed: Feb. 14, 2013

(86) PCT No.: PCT/JP2013/053500
§ 371 (c)(1),
(2) Date: Aug. 11, 2014

(87) PCT Pub. No.: WO2013/122130
PCT Pub. Date: Aug. 22, 2013

(65) Prior Publication Data
US 2015/0011766 A1    Jan. 8, 2015

(30) Foreign Application Priority Data
Feb. 17, 2012    (JP) ................................ 2012-032400

(51) Int. Cl.
| | |
|---|---|
| *C07D 211/18* | (2006.01) |
| *C07F 5/02* | (2006.01) |
| *C07C 231/02* | (2006.01) |
| *C07D 211/16* | (2006.01) |
| *B01J 31/14* | (2006.01) |
| *B01J 31/02* | (2006.01) |
| *C07B 43/06* | (2006.01) |

(52) U.S. Cl.
CPC .......... *C07C 231/02* (2013.01); *B01J 31/0275* (2013.01); *B01J 31/146* (2013.01); *C07B 43/06* (2013.01); *C07D 211/16* (2013.01); *C07F 5/025* (2013.01); *B01J 2231/44* (2013.01); *C07C 2101/20* (2013.01); *C07D 211/18* (2013.01)

(58) Field of Classification Search
CPC .............................. C07D 211/18; C07F 5/025
USPC ....................................................... 546/13
See application file for complete search history.

(56) References Cited

U.S. PATENT DOCUMENTS

| | | | |
|---|---|---|---|
| 2003/0216287 A1 | 11/2003 | Tang | |
| 2004/0010162 A1 | 1/2004 | Petasis et al. | |
| 2010/0197960 A1 | 8/2010 | Hall et al. | |
| 2011/0319620 A1 | 12/2011 | Ishihara et al. | |

FOREIGN PATENT DOCUMENTS

| | | | | |
|---|---|---|---|---|
| JP | A-61-000050 | 1/1986 | | |
| JP | A-2002-265472 | 9/2002 | | |
| JP | A-2004-506711 | 3/2004 | | |
| JP | A-2010-538021 | 12/2010 | | |
| WO | WO 2004/113351 A2 | 12/2004 | | |
| WO | WO 2010/103976 A1 | 9/2010 | | |
| WO | WO 2012/109749 A1 * | 2/2012 | ............ | C07C 231/02 |
| WO | WO 2012/109749 A1 | 8/2012 | | |

OTHER PUBLICATIONS

Ishihara et al., "3,4,5-Trifluorobenzeneboronic Acid as an Extremely Active Amidation Catalyst", *J. Org. Chem.*, 1996, pp. 4196-4197, vol. 61.

King et al., "Defining the Structural Parameters That Confer Anticonvulsant Activity by the Site-by-Site Modification of (R)-N'-Benzyl 2-Amino-3-methylbutanamide", *Journal of Medicinal Chemistry*, Aug. 2011, pp. 6432-6442, vol. 54.

Maki et al., "New boron(III)-catalyzed amide and ester condensation reactions", *Tetrahedron*, 2007, pp. 8645-8657, vol. 63.

Tang, "Boric Acid Catalyzed Amide Formation From Carboxylic Acids and Amines: N-Benzyl-4-Phenylbutyramide", *Organic Syntheses*, 2005, pp. 262, vol. 81.

(Continued)

*Primary Examiner* — Kamal Saeed
*Assistant Examiner* — Janet L Coppins
(74) *Attorney, Agent, or Firm* — Oliff PLC

(57) ABSTRACT

A method for production of hydroxycarboxylic acid amide compounds, including performing amide condensation between an α- or β-hydroxycarboxylic acid compound and an amine compound in the presence as a catalyst of an alkylboronic acid represented by $R^3B(OH)_2$ (wherein $R^3$ is a primary alkyl group) or an arylboronic acid compound to produce a hydroxycarboxylic acid amide compound, the arylboronic acid compound being represented by Formula (1):

[Chem. 1]

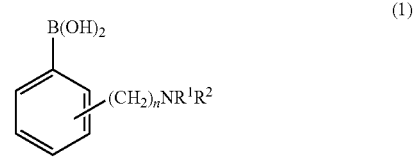

(1)

(in Formula (1), $-(CH_2)_n NR^1R^2$ is bonded at an ortho position or a para position, n is 1 or 2, $R^1$ is a tertiary alkyl group, $R^2$ is a secondary or tertiary alkyl group, and $-NR^1R^2$ may be a ring).

7 Claims, No Drawings

(56) References Cited

OTHER PUBLICATIONS

Myla Varapu et al., "Boric Acid Catalyzed Amidation in the Synthesis of Active Pharmaceutical Ingredients", *Organic Process Research & Development*, 2007, pp. 1065-1068, vol. 11, No. 6.

Peçanha et al., "Synthesis and anti-HIV activity of new C$_2$ symmetric derivatives designed as HIV-1 protease inhibitors", *Il Farmaco*, 2003, pp. 149-157, vol. 58.

Agwada, "Potential Central Nervous System Active Agents. 1. Synthesis of Aromatic N-Benzyl Amides", *Journal of Chemical and Engineering Data*, 1982, pp. 479-481, vol. 27, No. 4.

Marcelli, "Mechanistic Insights into Direct Amide Bond Formation Catalyzed by Boronic Acids: Halogens as Lewis Bases", *Agnew. Chem. Int. Ed.*, 2010, pp. 6840-6843, vol. 49.

International Search Report issued in International Patent Application No. PCT/JP2013/053500 mailed May 7, 2013 (with translation).

\* cited by examiner

METHOD FOR PRODUCTION OF HYDROXYCARBOXYLIC ACID AMIDE COMPOUNDS AND NOVEL ARYLBORONIC ACID COMPOUND

TECHNICAL FIELD

The present invention relates to a method for the production of hydroxycarboxylic acid amide compounds and to a novel arylboronic acid compound.

BACKGROUND ART

Amide condensation using arylboronic acid catalysts is heretofore known. For example, Patent Literature 1, on page 39, describes arylboronic acid catalysts such as 2-(diisopropylaminomethyl)phenylboronic acid and 2-(2,2,6,6-tetramethylpiperidinylmethyl)phenylboronic acid, and, on pages 42 and 43, describes a reaction example in which a carboxylic acid compound and an amine compound are subjected to amide condensation catalyzed by 2-(diisopropylaminomethyl)phenylboronic acid to give the corresponding carboxylic acid amide compound.

Further, in Non Patent Literature 1, a reaction example is described in which the amide condensation between a carboxylic acid compound and an amine compound is catalyzed by 3,4,5-trifluorophenylboronic acid that is an arylboronic acid compound having an electron-withdrawing substituent to produce the corresponding carboxylic acid amide compound. For example, a carboxylic acid amide compound substantially free from racemization is shown to be obtained in high yield by the amide condensation between an optically active α-hydroxycarboxylic acid compound and benzylamine under toluene reflux.

CITATION LIST

Patent Literature

PTL 1: International Publication No. WO 2004/113351

Non Patent Literature

NPL 1: J. Org. Chem., 1996, vol. 61, pp. 4196-4197

SUMMARY OF INVENTION

Technical Problem

However, Patent Literature 1 does not consider the amide condensation between an α-hydroxycarboxylic acid compound and an amine compound, and does not describe or suggest any structures of catalysts useful for the amide condensation between such compounds. While on the other hand Non Patent Literature 1 describes an amide condensation reaction between an α-hydroxycarboxylic acid compound and an amine compound, 3,4,5-trifluorophenylboronic acid is the only catalyst that is used in the disclosed reaction. Thus, this literature fails to describe or suggest the probability that there would or would not be any catalysts that outperform 3,4,5-trifluorophenylboronic acid in terms of catalytic activity or versatility in such amide condensation, needless to mention the structures of such catalysts.

The present invention has been made in order to solve such problems in the art. It is therefore a main object of the invention to provide techniques associated with the amide condensation between an α- or β-hydroxycarboxylic acid compound and an amine compound that can produce a carboxylic acid amide compound with a higher yield than heretofore achieved and are applicable to a wide range of reaction substrates.

Solution to Problem

To achieve the above object, the present inventors studied the amide condensation between an α- or β-hydroxycarboxylic acid compound and an amine compound under catalysis of alkylboronic acids or arylboronic acid compounds having various structures. As a result, the present inventors have found that high yield and high applicability to a wide range of reaction substrates are obtained by the use of alkylboronic acids having a non-branched alkyl group or arylboronic acid compounds having a specific aminoalkyl group at an ortho position. The present invention has been completed based on the finding.

A method for production of carboxylic acid amide compounds of the invention includes performing amide condensation between an α- or β-hydroxycarboxylic acid compound and an amine compound in the presence as a catalyst of an alkylboronic acid represented by $R^3B(OH)_2$ (wherein $R^3$ is a primary alkyl group) or an arylboronic acid compound represented by Formula (1) (in Formula (1), —$(CH_2)_nNR^1R^2$ is bonded at an ortho position or a para position, n is 1 or 2, $R^1$ is a tertiary alkyl group, $R^2$ is a secondary or tertiary alkyl group, and —$NR^1R^2$ may be a ring) to produce a hydroxycarboxylic acid amide compound.

[Chem. 1]

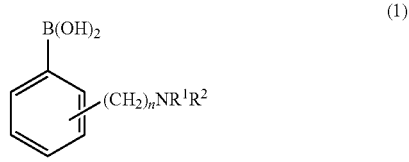

(1)

A novel arylboronic acid compound of the invention is represented by Formula (2):

[Chem. 2]

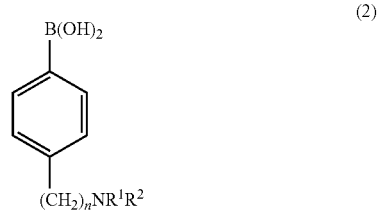

(2)

(in Formula (2), n is 1 or 2, $R^1$ is a tertiary alkyl group, $R^2$ is a secondary or tertiary alkyl group, and —$NR^1R^2$ may be a ring).

Advantageous Effects of Invention

The inventive method for the production of carboxylic acid amide compounds not only achieves higher yields of carboxylic acid amide compounds than heretofore obtained but also is applicable to a wide range of reaction substrates. These effects are probably ascribed to the following reasons (see the formula below). The formula below illustrates a reaction example involving 2-(2,2,6,6-tetramethylpiperidinylmethyl)

phenylboronic acid as the arylboronic acid compound, mandelic acid as the hydroxycarboxylic acid compound, and phenylethylamine as the amine compound. First, the hydroxycarboxylic acid compound reacts with the arylboronic acid compound and readily forms the intermediate shown in the formula. Subsequently, the bulky amino group of the arylboronic acid compound activates the amine compound and this facilitates for the amine compound to nucleophilically attack the intermediate, resulting in the formation of a hydroxycarboxylic acid amide compound and the arylboronic acid compound. As a result of this easy formation of the intermediate and also the nucleophilic amine compound attack facilitated by the arylboronic acid compound, the reactivity is increased. These are probably the reasons why the inventive method achieves higher yields of carboxylic acid amide compounds and is applicable to a wider range of reaction substrates.

n is 1 or 2. In view of the availability of the arylboronic acid compounds, n is preferably 1. $R^1$ is a tertiary alkyl group, $R^2$ is a secondary or tertiary alkyl group, and —$NR^1R^2$ may be a ring. Preferred examples of the secondary alkyl groups include secondary alkyl groups having 3 to 20 carbon atoms such as isopropyl group, sec-butyl group, sec-pentyl group, sec-hexyl group, cyclopropyl group, cyclobutyl group, cyclopentyl group and cyclohexyl group. Preferred examples of the tertiary alkyl groups include tertiary alkyl groups having 4 to 20 carbon atoms such as tert-butyl group, tert-pentyl group and tert-hexyl group. When —$NR^1R^2$ is a ring, the nitrogen-containing hetero ring is preferably such that both the carbon atoms adjacent to the nitrogen atom have one or two alkyl groups. Examples of such structures include 2,2,6,6-tetramethylpiperidinyl group, 2,2,6-trimethylpiperidinyl group, 2,2,5,5-tetramethylpyrrolidinyl group and 2,2,5-trimethylpyrrolidinyl group.

[Chem. 3]

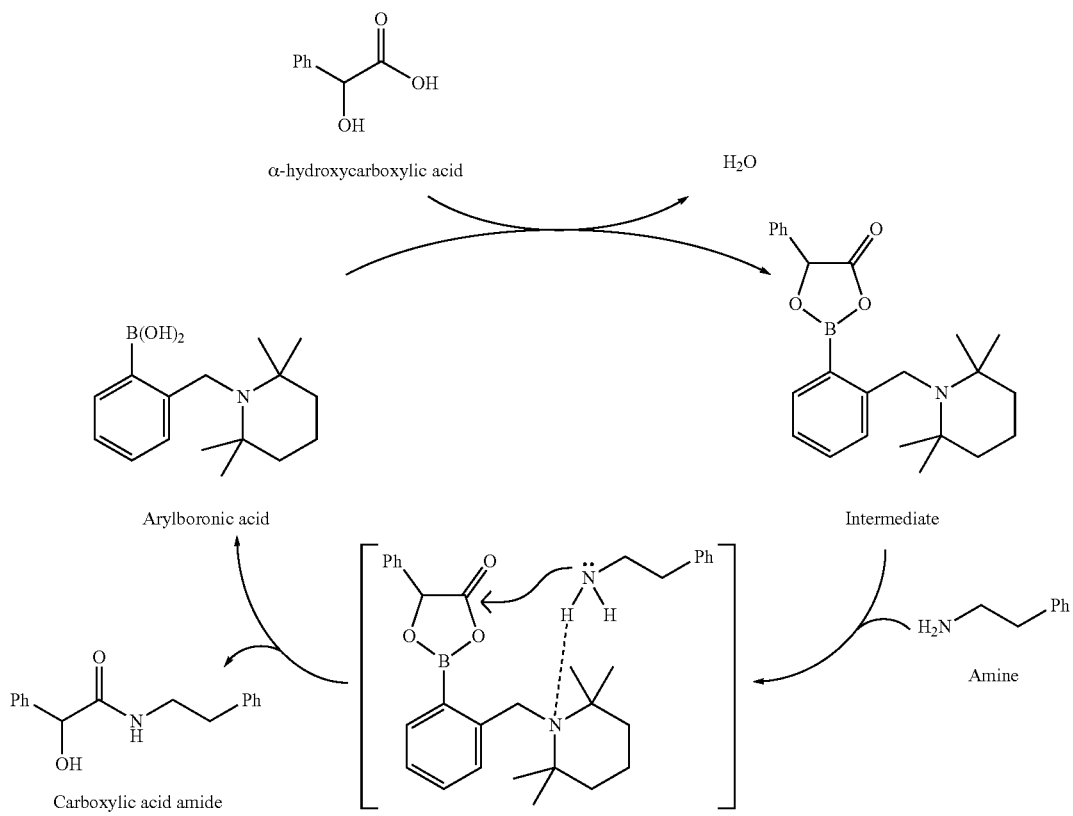

DESCRIPTION OF EMBODIMENTS

A method for production of carboxylic acid amide compounds of the invention includes performing amide condensation between an α- or β-hydroxycarboxylic acid compound and an amine compound in the presence as a catalyst of an alkylboronic acid represented by $R^3B(OH)_2$ (wherein $R^3$ is a primary alkyl group) or an arylboronic acid compound represented by the above Formula (1) to produce a hydroxycarboxylic acid amide compound.

$R^3$ is a primary alkyl group and is preferably a primary alkyl group having 1 to 20 carbon atoms. Examples include methyl group, ethyl group, n-propyl group, n-butyl group, isobutyl group and n-pentyl group. Of these, methyl group and n-butyl group are particularly preferable. In Formula (1), In the inventive method for the production of carboxylic acid amide compounds, the α- or β-hydroxycarboxylic acid compound that is a reaction substrate is not particularly limited as long as the carboxylic acid compound has a hydroxyl group at the α position or the β position. For example, the α-hydroxycarboxylic acid may be represented by RCH(OH)COOH (wherein R is an alkyl group or an aryl group). In this case, the alkyl group is preferably one having 1 to 20 carbon atoms, with examples including methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, hexyl group, isohexyl group, sec-hexyl group, tert-hexyl group, neohexyl group, heptyl group, octyl group, bis (2-ethylhexyl) group, decyl group, cetyl group, cyclopropyl group, cyclobutyl group, cyclopentyl group and cyclohexyl group. Examples of the aryl groups include phenyl group, tolyl group, xylyl group and naphthyl group. These alkyl groups and aryl groups may have substituents appropriately. Examples of the substituents include halogens, cyano group and nitro group. It is possible to use optically active α-hydroxycarboxylic acids in which the carbon atom bonded to the hydroxyl group is asymmetric. In this case, the carboxylic acid amide compounds obtained by the inventive production method maintain the optical activity. Specific examples of the β-hydroxycarboxylic acids include salicylic acid.

In the inventive method for the production of carboxylic acid amide compounds, the amine compound that is another reaction substrate is a primary amine or a secondary amine. Examples of the primary amines include alkylamines such as methylamine, ethylamine, n-propylamine, isopropylamine, n-butylamine, isobutylamine, sec-butylamine, tert-butylamine, n-pentylamine, isopentylamine, sec-pentylamine, tert-pentylamine and neopentylamine; cycloalkylamines such as cyclopropylamine, cyclobutylamine, cyclopentylamine, cyclohexylamine and cyclododecylamine; aralkylamines such as benzylamine, phenethylamine and benzhydrylamine; and arylamines such as aniline and naphthylamine. Examples of the secondary amines include dialkylamines such as dimethylamine, diethylamine, di-n-propylamine, diisopropylamine, di-n-butylamine, diisobutylamine, di-sec-butylamine, di-tert-butylamine, di-n-pentylamine, diisopentylamine, di-sec-pentylamine, di-tert-pentylamine, dineopentylamine, methylethylamine and isopropylethylamine; dicycloalkylamines such as dicyclopropylamine, dicyclobutylamine, dicyclopentylamine, dicyclohexylamine and dicyclododecylamine; diaralkylamines such as dibenzylamine and diphenethylamine; diarylamines such as diphenylamine and dinaphthylamine; and cyclic amines such as piperidine, pyrrolidine and morpholine. These primary and secondary amines may have substituents appropriately. Examples of the substituents which may be present on the alkyl groups include halogens, cyano group and nitro group. Examples of the substituents which may be present on the cycloalkyl groups, the aralkyl groups, the aryl groups and the cyclic amines include halogens, alkyl groups, cyano group and nitro group.

The inventive method for the production of carboxylic acid amide compounds is useful when the hydroxycarboxylic acid compounds and the amine compounds have low reactivity. Exemplary hydroxycarboxylic acid compounds having low reactivity are those represented by RCH(OH)COOH in which R is a long-chain alkyl group (for example, n-hexyl group). Exemplary amine compounds having low reactivity are secondary amines (for example, di-n-butylamine and piperidine) and some of the primary amines such as cycloalkylamines (for example, cyclododecylamine) and arylamines (for example, aniline). In the case where the amide condensation using these low-reactive substrates is catalyzed by 3,4,5-trifluorophenylboronic acid described in Non Patent Literature 1, the reaction does not substantially take place or only proceeds to such an extent that the yield of the carboxylic acid amide compound is low. In contrast, the use of the arylboronic acid compound of Formula (1) as the catalyst allows the amide condensation to readily proceed to afford the carboxylic acid amide compound in high yield.

In the inventive method for the production of carboxylic acid amide compounds, the amide condensation is preferably performed under weakly acidic conditions (pH 4 to 5). The arylboronic acid compounds of Formula (1) are prone to be decomposed under neutral to basic conditions and may fail to allow the amide condensation to proceed sufficiently. Weakly acidic conditions eliminate (or reduce) such concerns. In this case, it is preferable that the hydroxycarboxylic acid compound be added in excess over the amine compound or the reaction be performed in the presence of an additional carboxylic acid compound (for example, an aromatic carboxylic acid such as benzoic acid) having lower reactivity than the hydroxycarboxylic acid compound. The former approach is preferably adopted when the hydroxycarboxylic acid compound is relatively inexpensive, and the latter approach is preferably selected when the hydroxycarboxylic acid compound is relatively expensive and the additional carboxylic acid compound is less expensive than the hydroxycarboxylic acid compound.

In the inventive method for the production of carboxylic acid amide compounds, the amount of the alkylboronic acid or the arylboronic acid compound used is preferably 0.1 to 50 mol %, and more preferably 1 to 20 mol % relative to 1 mol of the amine compound.

In the inventive method for the production of carboxylic acid amide compounds, the reaction solvent is not particularly limited as long as the solvent does not adversely affect the amide condensation. Preferred examples include hydrocarbon solvents, alcohol solvents, nitrile solvents and nitro solvents. Examples of the hydrocarbon solvents include hexane, heptane, octane, nonane, toluene and xylene. A small amount of water may be added to the hydrocarbon solvent. The addition of water may enhance the reproducibility of the reaction. Examples of the alcohol solvents include isopropyl alcohol. Examples of the nitrile solvents include butyronitrile and propionitrile. Examples of the nitro solvents include nitromethane and nitroethane. A mixture of these solvents may be used. Hydroxycarboxylic acids and amines having high polarity exhibit poor solubility in hydrocarbon solvents. When such substrates are used, the reaction preferably involves an alcohol solvent such as isopropyl alcohol to ensure smooth progress of the reaction.

In the inventive method for the production of carboxylic acid amide compounds, the reaction temperature may be selected appropriately in light of conditions such as the reaction rate. For example, the reaction temperature is preferably selected in the range of 20 to 200° C., and more preferably in the range of 60 to 160° C. In the amide condensation, water is formed in addition to the carboxylic acid amide compound. To increase the yield of the carboxylic acid amide compound, performing dehydration in an efficient manner is preferable. For example, it is preferable that the reaction temperature be set at the reflux temperature (namely, the boiling point) of the solvent and the solvent be refluxed while performing azeotropic dehydration.

In the inventive method for the production of carboxylic acid amide compounds, the reaction time may be determined appropriately in accordance with conditions such as the reaction substrates and the reaction temperature. The reaction time is usually several minutes to several tens of hours. The amide condensation may be performed until the reaction substrates are completely consumed. In the case where the rate of consumption of the reaction substrates becomes extremely slow with the progress of the reaction, it may be preferable at times to terminate the reaction and collect the carboxylic acid amide compound even when the consumption of the reaction substrates is incomplete.

In the inventive method for the production of carboxylic acid amide compounds, the target carboxylic acid amide compound may be isolated by a known isolation method. For example, the reaction mixture may be concentrated by evaporating the reaction solvent under reduced pressure and thereafter the target carboxylic acid amide compound may be isolated by a purification method such as column chromatography or recrystallization.

EXAMPLES

Reference Example

The procedures for synthesizing 2-(2,2,6,6-tetramethylpiperidinylmethyl)phenylboronic acid used as a catalyst (hereinafter, written as the catalyst C) will be described below. This compound is a known compound.

First, a flask was loaded with 2-bromobenzyl bromide (10 mmol), potassium carbonate (22 mmol), potassium iodide (11 mmol), 3-pentanone (20 mL) and 2,2,6,6-tetramethylpiperidine (22 mmol). The mixture was heated under reflux for 2 days. After being allowed to cool to room temperature, the mixture was filtered to remove the insolubles. The filtrate was washed with water 2 times, and the aqueous phases were each extracted with chloroform. The organic phases were combined together, dried with sodium sulfate, and concentrated under reduced pressure. The resultant crude product was purified by column chromatography (NH silica gel, hexane), thereby obtaining the target amine compound, namely, 1-bromo-2-(2,2,6,6-tetramethylpiperidinylmethyl)benzene in 92% yield.

Next, TMEDA (20 mmol) was added to a solution of the amine compound (10 mmol) in THF (8.5 mL). The resultant solution was cooled to −78° C. A 1.5 M BuLi hexane solution (30 mmol) was slowly added dropwise to the solution. After the resultant solution was stirred for 1.5 hours at −78° C., B(OMe)$_3$ (60 mmol) was added. The temperature was raised to room temperature, and stirring was performed for 8 hours. Water was added to this reaction mixture, and stirring was performed for another 15 minutes. The mixture was washed with water, and the aqueous phase was extracted with chloroform. All the organic phases were combined together, dried with sodium sulfate, and concentrated under reduced pressure to give the target catalyst C.

Experimental Examples 1 to 12

With use of various catalysts shown in Table 1, the amide condensation between mandelic acid and 2-phenylethylamine was performed to obtain the corresponding carboxylic acid amide compound. The synthesis procedures will be described below. A 20 mL flask was loaded with 2-phenylethylamine (2.5 mmol), mandelic acid (2.5 mmol or 3.0 mmol), the catalyst (see Table 1, 0.25 mmol) and toluene (10 mL). A column packed with dried molecular sieve 3A (approximately 3 g) (a small-size Soxhlet extractor) was attached to the flask. The solution was heated and dehydrated under reflux for 8 hours (oil bath temperature: approximately 130° C.). Thereafter, the solution was allowed to cool to room temperature, and toluene was evaporated under reduced pressure. The resultant crude product was purified by column chromatography (silica gel, hexane-ethyl acetate 3:1). Thus, the target carboxylic acid amide compound was obtained. The results are described in Table 1. Experimental Examples 5 and 6 correspond to Inventive Examples, and the other Experimental Examples are Comparative Examples.

TABLE 1

| Experimental example | Catalyst Code | Catalyst Formula | Mandelic acid (equiv) | Yield (%) | Decomposition of catalyst (%) |
|---|---|---|---|---|---|
| 1 | A | B(OH)$_2$ (structure) | 1.0 | 17 | |
| 2 | A | | 1.2 | 34 | |
| 3 | B | B(OH)$_2$ (structure) | 1.0 | 37 | |
| 4 | B | | 1.2 | 44 | |

TABLE 1-continued

| | | | | | |
|---|---|---|---|---|---|
| 5 | C | B(OH)₂ with 2,2,6,6-tetramethylpiperidinylmethyl at ortho position | 1.0 | 80 | 41 |
| 6 | | | 1.2 | 97 | ~0 |
| 7 | D | B(OH)₂ with 2,2,6,6-tetramethylpiperidinylmethyl groups at both ortho positions | 1.0 | 69 | 54 |
| 8 | | | 1.2 | 82 | 16 |
| 9 | E | B(OH)₂ with F atoms at 3,4,5 positions | 1.0 | 58 | |
| 10 | | | 1.2 | 74 | |
| 11 | F | B(OH)₃ | 1.0 | 6 | |
| 12 | | | 1.2 | 30 | |

As apparent from Table 1, Experimental Examples 5 and 6 involving the catalyst C resulted in higher reaction activity and afforded the carboxylic acid amide compound with a higher yield compared to Experimental Examples 1 to 4 and 7 to 12 which used the catalysts A, B, D, E and F. Specifically, the reaction promoting effect was smaller than the catalyst C in the case of the catalysts A and B which had a diisopropylaminomethyl group(s) at either or both of the ortho positions of phenylboric acid, and also the catalyst F which was boric acid. The catalyst D which had 2,2,6,6-tetramethylpiperidinylmethyl groups at both the ortho positions of phenylboric acid, and the catalyst E which had fluorine atoms at the 3, 4 and 5 positions of phenylboric acid exhibited slightly lower reaction promoting effect than the catalyst C. In contrast, the catalyst C which had a 2,2,6,6-tetramethylpiperidinylmethyl group at one of the ortho positions of phenylboric acid outperformed the other catalysts in terms of reaction promoting effect. This compound represents an embodiment in which two tertiary alkyl groups are bonded to the nitrogen atom.

From the comparison of examples which used the catalyst C, Experimental Example 5 involving the equimolar amounts of mandelic acid and 2-phenylethylamine resulted in 41% decomposition of the catalyst C, whilst the decomposition of the catalyst C was suppressed to almost zero in Experimental Example 6 in which the molar amount of mandelic acid was 1.2 times greater than that of 2-phenylethylamine and consequently the reaction mixture was rendered weakly acidic. In this regard, the results were different in examples in which the catalyst D was used. Specifically, Experimental Example 7 involving the equimolar amounts of mandelic acid and 2-phenylethylamine resulted in 54% decomposition of the catalyst D; however, the use of mandelic acid in a molar amount 1.2 times greater than that of 2-phenylethylamine in Experimental Example 8 reduced the decomposition of the catalyst D only to 16%, although the excessive acid use rendered the reaction mixture weakly acidic. The decomposition products of the catalysts C and D had —H instead of —B(OH)₂.

Experimental Examples 13 to 48

With use of the various catalysts shown in Table 2 and Table 3, the amide condensation between various α-hydroxycarboxylic acid compounds and various amine compounds was performed to obtain the corresponding carboxylic acid amide compounds. The synthesis procedures were similar to those in Experimental Examples 1 to 12, except that the reaction in Experimental Example 15 was performed under weakly acidic conditions by adding benzoic acid (1.0 equivalent) and that the reaction in Experimental Example 47 was performed in xylene (boiling point 144° C.) under weakly acidic conditions by adding benzoic acid (0.10 equivalent). The results are described in Table 2 and Table 3. Experimental Examples 14, 15, 19, 22, 26, 32, 37, 40, 43, 46 and 47 correspond to Inventive Examples, and the other Experimental Examples are Comparative Examples.

TABLE 2
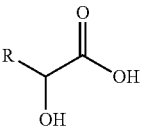
| Experimental example | α-hydroxycarboxylic acid | Amine | Catalyst | Time (h) | Yield (%) |
|---|---|---|---|---|---|
| 13 | | | A | 14 | 9 |
| 14 | | | C | 14 | 46 |
| 15 | | | C* | 16 | 99 |
| 16 | | | D | 14 | 9 |
| 17 | | | E | 14 | 0 |
| 18 | | | A | 12 | 29 |
| 19 | | | C | 12 | 74 |
| 20 | | | E | 12 | 30 |
| 21 | | | A | 5 | 81 |
| 22 | | | C | 5 | 99 |
| 23 | | | E | 5 | 78 |
| 24 | | | A | 3 | 34 |
| 25 | | | B | 3 | 60 |
| 26 | | | C | 3 | 95 |
| 27 | | | D | 3 | 74 |
| 28 | | | E | 3 | 66 |
| 29 | | | F | 3 | 22 |
| 30 | | | A | 8 | 39 |
| 31 | | | B | 8 | 27 |
| 32 | | | C | 8 | 51 |
| 33 | | | D | 8 | 30 |
| 34 | | | E | 8 | 0 |
| 35 | | | F | 8 | 0 |
*The reaction was conducted in the presence of benzoic acid (1.0 equivalent)

TABLE 3

α-hydroxycarboxylic acid (1.2 equiv) + HNR'R'' (Amine 2.5 mmol) → Carboxylic acid amide
Catalyst (10 mol %), Toluene (10 mL), Heated and dehydrated under reflux

| Experimental example | α-hydroxycarboxylic acid | Amine | Catalyst | Time (h) | Yield (%) |
|---|---|---|---|---|---|
| 36 | 2-hydroxyisobutyric acid (2,2-dimethyl, α,α-dihydroxy) | H₂N-CH₂CH₂-Ph (2-phenylethylamine) | A | 16 | 81 |
| 37 | | | B | 14 | 99 |
| 38 | | | C | 14 | 99 |
| 39 | 3-phenyl-2-hydroxy propanoic acid (α,α-dihydroxy) | H₂N-CH₂CH₂-Ph | A | 5 | 63 (100% ee) |
| 40 | | | C | 5 | >99 (100% ee) |
| 41 | | | E | 5 | 68 |
| 42 | 3-phenyl-2-hydroxy propanoic acid | 3,5-dimethylpiperidine | A | 18 | 50 |
| 43 | | | C | 18 | 99 |
| 44 | | | E | 18 | 22 |
| 45 | 3-phenyl-2-hydroxy propanoic acid | HN(nBu)₂ | A | 17 | 5 |
| 46 | | | C | 17 | 23 |
| 47 | | | C* | 8 | 77 |
| 48 | | | E | 15 | 0 |

*The reaction was conducted in xylene (boiling point 144° C.) in the presence of benzoic acid (0.10 equivalent)

As apparent from Table 2 and Table 3, the catalyst C exhibited excellent reaction activity in all of the amide condensation reactions. This result shows that the catalyst C can favor the amide condensation of a wider range of α-hydroxycarboxylic acid compounds and amine compounds as the reaction substrates to give higher yields of the carboxylic acid amide compounds than the other catalysts.

Specifically, Experimental Examples 13, 14, 16 and 17 will be discussed in which mandelic acid was used as the α-hydroxycarboxylic acid compound and 3,5-dimethylpiperidine which was a low-reactive secondary amine was used as the amine compound. While the catalysts A and D provided less than 10% yield and the catalyst E gave no yield, the catalyst C achieved a yield of 46%. In particular, although the catalysts D and E gave relatively high yields in the amide condensation reactions shown in Table 1 (in which the amine compound used was 2-phenylethylamine that was a primary amine), the reactions catalyzed here by these catalysts resulted in low yields, indicating applicability to a limited range of reaction substrates. In order to suppress the decomposition of the catalyst C, benzoic acid, which was less expensive than mandelic acid was added in Experimental Example 15. This addition achieved a marked effect and the yield was increased to 99%. These results show that the catalyst C can easily promote the amide condensation even in the case where a secondary amine is used as the amine compound.

In Experimental Examples 18 to 20, mandelic acid was used as the α-hydroxycarboxylic acid compound and cyclododecylamine having a bulky alkyl group was used as the amine compound. While the catalysts A and E gave as low a yield as approximately 30%, the catalyst C achieved a yield of 74% and exhibited a higher reaction promoting effect compared to the other catalysts.

In Experimental Examples 21 to 23, mandelic acid was used as the α-hydroxycarboxylic acid compound and benzhydrylamine was used as the amine compound. The catalysts A and E gave a relatively high yield of approximately 80%, but the catalyst C exhibited a still higher reaction promoting effect and achieved a yield of 99%.

In Experimental Examples 24 to 29, 2-hydroxyoctanoic acid was used as the α-hydroxycarboxylic acid compound and 2-phenylethylamine was used as the amine compound. The yield was increased in the order of the catalyst F, the catalyst A, the catalyst B, the catalyst E, the catalyst D and the catalyst C. In this amide condensation, the catalyst C gave a yield of 95% and exhibited a higher reaction promoting effect than the other catalysts.

In Experimental Examples 30 to 35, 2-hydroxyoctanoic acid was used as the α-hydroxycarboxylic acid compound and low-reactive aniline was used as the amine compound. The catalysts E and F did not substantially favor the reaction. The other catalysts allowed the reaction to proceed with an increasing yield in the order of the catalyst B, the catalyst D, the catalyst A and the catalyst C. In this amide condensation, the catalyst C gave a yield of 51% and exhibited a higher reaction promoting effect than the other catalysts.

In Experimental Examples 36 to 38, 2-hydroxyisobutyric acid was used as the α-hydroxycarboxylic acid compound and 2-phenylethylamine was used as the amine compound. All the catalysts A, C and E gave a yield higher than 80%. The catalyst C and the catalyst E exhibited a high reaction promoting effect to give the carboxylic acid amide compound in 99% yield.

In Experimental Examples 39 to 41, optically active 2-hydroxy-3-phenylpropionic acid was used as the α-hydroxycarboxylic acid compound and 2-phenylethylamine was used as the amine compound. Both the catalysts A and E gave a yield between 60 and 70%. In contrast, the catalyst C gave a quantitative yield of the carboxylic acid amide compound without any loss of the optical purity.

In Experimental Examples 42 to 44, 2-hydroxy-3-phenylpropionic acid was used as the α-hydroxycarboxylic acid compound and secondary amine 3,5-dimethylpiperidine was used as the amine compound. While the catalysts E and A gave yields of 22% and 50%, respectively, the catalyst C afforded the carboxylic acid amide compound quantitatively.

In Experimental Examples 45, 46 and 48, 2-hydroxy-3-phenylpropionic acid was used as the α-hydroxycarboxylic acid compound and di-n-butylamine that was a secondary amine was used as the amine compound. The catalyst E did not show any activity, and the catalyst A gave poor yield of 5%. In contrast, the catalyst C gave a yield of 23%. In Experimental Example 47, the reaction was catalyzed by the catalyst C in the presence of a small amount of benzoic acid, resulting in a higher yield of 77%.

Experimental Example 49

Experimental Example 14 has illustrated that the catalyst C catalyzed the reaction of mandelic acid as the α-hydroxycarboxylic acid compound and secondary amine 3,5-dimethylpiperidine as the amine compound in a quantitative manner. In Experimental Example 49, the amide condensation was performed under the same reaction conditions as in Experimental Example 14 except that 2-phenylpropionic acid was used instead of mandelic acid as illustrated below. As a result, the corresponding carboxylic acid amide compound was obtained only in 18% yield. This result shows that the catalyst C does not favor the amide condensation of all kinds of carboxylic acid compounds and amine compounds but specifically promotes the amide condensation between α-hydroxycarboxylic acid compounds and amine compounds. Experimental Example 49 corresponds to Comparative Example in the invention.

[Chem. 4]

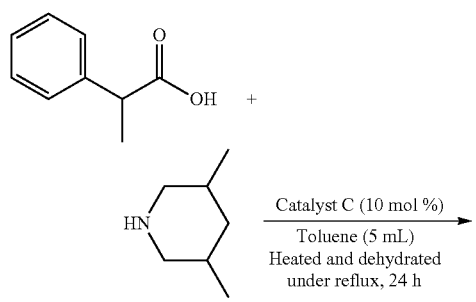

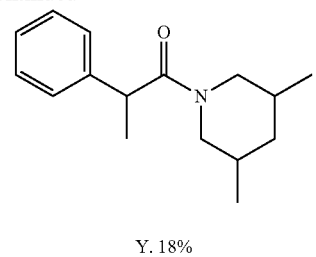

Y. 18%

The results of the above Experimental Examples show that the catalyst C can catalyze the amide condensation of a wider range of α-hydroxycarboxylic acid compounds and amine compounds as the reaction substrates and can achieve higher yields of the carboxylic acid amide compounds than the other catalysts. It has been further demonstrated that the catalyst C does not favor the amide condensation of all kinds of carboxylic acid compounds and amine compounds but specifically promotes the amide condensation between α-hydroxycarboxylic acid compounds and amine compounds. Furthermore, it has been shown that the decomposition of the catalyst C can be effectively suppressed under weakly acidic conditions (for example, when the α-hydroxycarboxylic acid compound is used in excess over the amine or when a low-reactive acid such as benzoic acid is added in addition to the α-hydroxycarboxylic acid compound).

Experimental Examples 50 to 54

The amide condensation between mandelic acid and 2-phenethylamine was performed while changing the amount of the catalyst as shown in Table 4. With a constant reaction time of 8 hours, the amount of the catalyst was decreased stepwise from 10 mol % to 1 mol %. The yield was reduced with decreasing amount of the catalyst. Even at 1 mol %, however, the reaction was allowed to proceed favorably when the reaction time was extended to 14 hours, to give the carboxylic acid amide compound in 98% yield. Experimental Examples 50 to 54 are all Inventive Examples.

TABLE 4

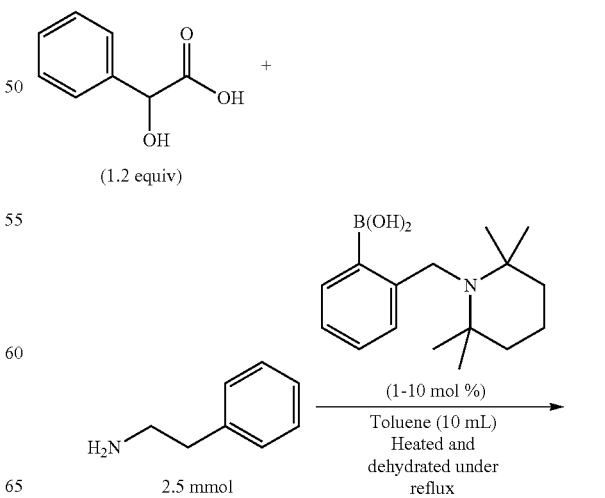

TABLE 4-continued

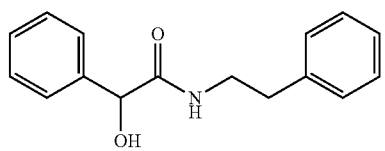 [SMILES: O=C(NCCc1ccccc1)C(O)c1ccccc1]

| Experimental example | Amount of catalyst (mol %) | Reaction time (h) | Yield (%) |
|---|---|---|---|
| 50 | 10 | 8 | 97 |
| 51 | 5 | 8 | 77 |
| 52 | 3 | 8 | 64 |
| 53 | 1 | 8 | 34 |
| 54 | 1 | 14 | 98 |

Experimental Examples 55 to 57

Catalysts having a tetramethylpiperidinylmethyl group at a meta position or a para position were synthesized. The catalytic activity in the amide condensation between mandelic acid and 3,5-dimethylpiperidine was studied as described in Table 5. As a result, the meta-substituted catalyst was decomposed even when benzoic acid (10 mol %) had been added, failing to afford the target carboxylic acid amide compound. In contrast, the ortho-substituted catalyst and the para-substituted catalyst were not decomposed and allowed the reaction to proceed favorably. Experimental Examples 55 and 57 correspond to Inventive Examples, and Experimental Example 56 is Comparative Example.

TABLE 5

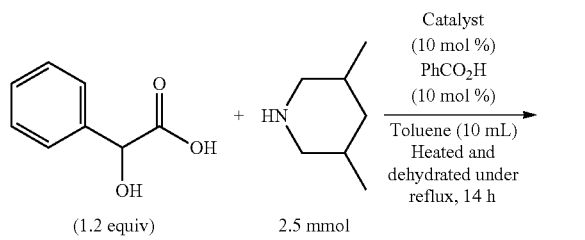

| Experimental example | Catalyst | Yield (%) | Decomposition of catalyst (%) |
|---|---|---|---|
| 55 | 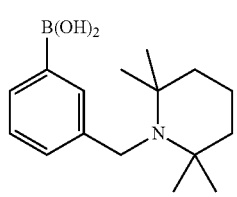 [SMILES: CC1(C)CCCC(C)(C)N1Cc1cccc(B(O)O)c1] | 85 | 0 |
| 56 | 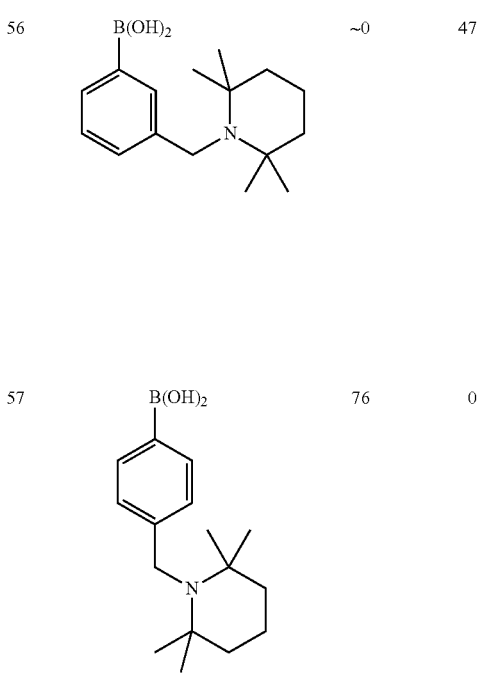 | ~0 | 47 |
| 57 | | 76 | 0 |

The meta-substituted catalyst and the para-substituted catalyst (see Examples 56 and 57 in Table 5) had been synthesized in accordance with the aforementioned procedures for the synthesis of the catalyst C, except that 3-bromobenzyl bromide or 4-bromobenzyl bromide was used instead of 2-bromobenzyl bromide. The para-substituted catalyst had a broad and complicated $^1$H NMR spectrum and consequently the identification of its structure was infeasible. Thus, the para-substituted catalyst was reacted with pinacol in toluene at room temperature for 30 minutes to convert the boronic acid moiety to a pinacol ester, and the structure of the resultant compound was identified. The $^1$H NMR data of the pinacol ester was as follows. $^1$H NMR (CDCl$_3$, 400 MHz) δ0.99 (s, 24H), 1.44-1.64 (m, 6H), 3.73 (s, 2H), 6.97 (d, J=7.8 Hz, 2H), 7.30 (d, J=7.8 Hz, 2H).

Experimental Example 58

The amide condensation between tartaric acid and benzylamine was studied (see the formula below). Since tartaric acid had high polarity, isopropyl alcohol (boiling point 82° C.) was used as the reaction solvent (oil bath temperature 100° C.). The reaction substrates were sufficiently dissolved in the solvent and the reaction took place favorably. Experimental Example 58 corresponds to Inventive Example.

[chem. 5]

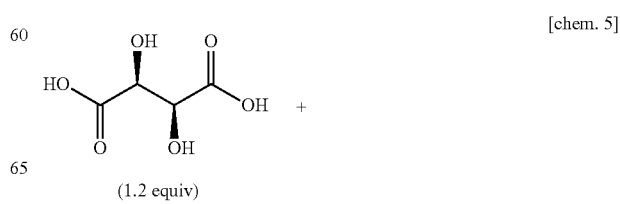

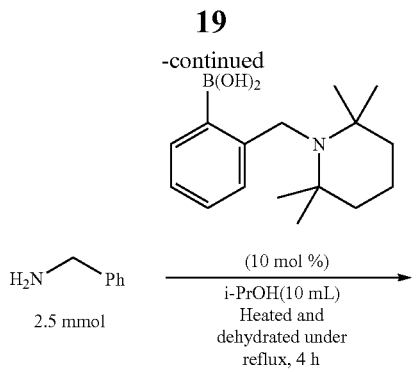

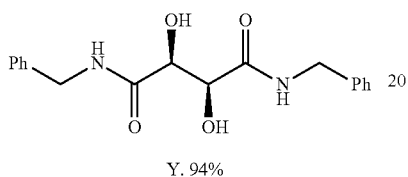

Experimental Examples 59 to 61

With use of various alkylboronic acids as catalysts, the amide condensation between mandelic acid and 3,5-dimethylpiperidine (1 equivalent) was performed as illustrated in Table 6 to study the catalytic activities. The procedures in the amide condensation will be described below based on Experimental Example 59. Mandelic acid (1.25 mmol), methylboronic acid (0.125 mmol) and benzoic acid (0.125 mmol) were weighed into a 20 mL flask and were dissolved in toluene (10 mL). To the solution, 3,5-dimethylpiperidine (1.25 mmol) and water (50 μL) were added, and the mixture was stirred at room temperature for 10 minutes. A column packed with dried molecular sieve 3A (approximately 2 g) (a small-size Soxhlet extractor) and a condenser tube were attached to the flask. The solution was heated and dehydrated under reflux for 14 hours (oil bath temperature: approximately 130° C.). Thereafter, the solution was cooled to room temperature, and toluene was evaporated under reduced pressure. The resultant crude product was purified by column chromatography (silica gel, hexane-ethyl acetate 3:1). Thus, 297 mg of the target amide compound was obtained (yield 96%). The results are described in Table 6. In Experimental Examples 60 and 61, the reaction was performed in the same manner as in Experimental Example 59 while using n-butylboronic acid and isopropylboronic acid, respectively, as the catalyst. The results are described in Table 6.

The study showed that methylboronic acid and n-butylboronic acid exhibited excellent catalytic activity in this reaction. On the other hand, the amide condensation catalyzed by isopropylboronic acid resulted in low yield. In the methylboronic acid-catalyzed reaction, higher reactivity was obtained when the reaction involved the addition of benzoic acid (10 mol %). Although not shown in Table 6, the addition of 50 mol % benzoic acid allowed the reaction to proceed favorably even when the amount of methylboronic acid was decreased to 1 mol %. Experimental Examples 59 and 60 correspond to Inventive Examples.

TABLE 6

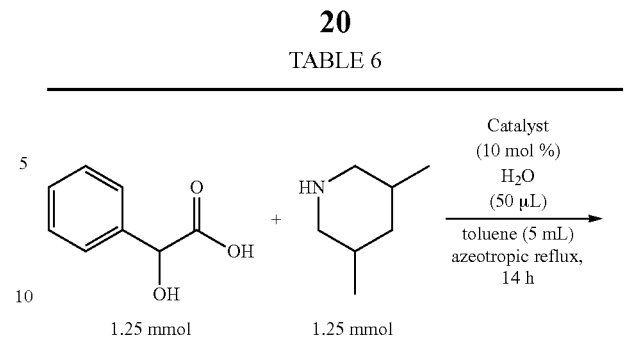

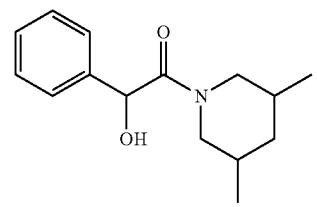 [SMILES: CC1CC(C)CN(C(=O)C(O)c2ccccc2)C1]

| Experimental example | Catalyst | Yield (%) |
|---|---|---|
| 59 | MeB(OH)$_2$ | 73 (96)* |
| 60 | n-BuB(OH)$_2$ | 89 |
| 61 | i-PrB(OH)$_2$ | 2 |

*The reaction was conducted in the presence of benzoic acid (10 mol %)

Experimental Examples 62 to 82

The amide condensation between various α-hydroxycarboxylic acids and various amines was performed with use of methylboronic acid catalyst. The synthesis procedures were similar to those in Experimental Example 59. The results are described in Table 7 and Table 8. The amide bond formation in (S)-3-phenyllactic acid took place without any racemization, and the corresponding amide was obtained in a high yield (Experimental Examples 62 to 68). The amide condensation of (R)-mandelic acid proceeded favorably but slight racemization occurred (Experimental Examples 69 to 75). This racemization was suppressed to some degree by using dichloroethane (boiling point 83° C.) as the reaction solvent. The condensation reactions involving high-reactive amines proceeded favorably even when the amount of the catalyst was decreased to 1 mol %. In the amide condensation reactions involving 2-hydroxyoctanoic acid, the corresponding amides were obtained in high yields (Experimental Examples 76 to 79). The amide condensation reactions between 2-hydroxyisobutyric acid having a quaternary carbon atom at the a position and a primary amine also afforded the corresponding amides in a high yield (Experimental Examples 80 to 82). Experimental Examples 62 to 82 correspond to Inventive Examples.

TABLE 7

$$R\text{-CH(OH)-COOH} + HN(R')(R'') \xrightarrow[\text{toluene (5 mL)}]{\substack{\text{MeB(OH)}_2 \text{ (X mol \%)} \\ \text{H}_2\text{O (50 μL)} \\ \text{azeotropic reflux}}} R\text{-CH(OH)-C(O)-N(R')(R'')}$$

1.25 mmol + 1.25 mmol

| Experimental example | Carboxylic acid | Amine | Amount of catalyst (mol %) | Time (h) | Yield (%) | |
|---|---|---|---|---|---|---|
| 62 | Ph-CH₂-CH(OH)-COOH (Ph, (S)) | H₂N-CH₂-Ph | 1 | 4 | 92 | 99% ee |
| 63 | " | H₂N-CH₂-CH₂-Ph | 1 | 10 | 93 | 99% ee |
| 64 | " | H₂N-CH(Ph)(Ph) | 1 | 10 | 87 | |
| 65 | " | HN(Me)-CH₂-Ph | 1 | 12 | 88 | |
| 66 | " | cyclododecyl-NH₂ | 10 | 12 | 79 (82)* | |
| 67 | " | 3,5-dimethylpiperidine (HN) | 10 | 4 | 66 (91)* | |
| 68 | " | HN(n-Bu)(n-Bu) | 10 | 24 | 76 (91)* | |
| 69 | Ph-CH(OH)-COOH | H₂N-CH₂-Ph | 1 | 24 | 82 | 94% ee |
| 70 | " | H₂N-CH₂-CH₂-Ph | 1 | 9 | 98 | 79% ee |
| 71 | " | H₂N-CH₂-CH₂-Ph | 1 | 22 | 63 | 94% ee† |
| 72 | " | H₂N-CH(Ph)(Ph) | 1 | 9 | 62 | |

TABLE 7-continued $$R-\underset{OH}{\underset{|}{CH}}-COOH + HN(R')(R'') \xrightarrow[\text{toluene (5 mL)}]{\text{MeB(OH)}_2 \text{ (X mol \%)}}_{\text{azeotropic reflux}} R-\underset{OH}{\underset{|}{CH}}-C(O)-N(R')(R'')$$

1.25 mmol    1.25 mmol

| Experimental example | Carboxylic acid | Amine | Amount of catalyst (mol %) | Time (h) | Yield (%) |
|---|---|---|---|---|---|
| 73 |  | HN(Me)CH$_2$Ph | 1 | 24 | 98 |
| 74 |  | cyclododecyl-NH$_2$ | 10 | 12 | 70 (97)* |
| 75 |  | HN(n-Bu)$_2$ | 10 | 24 | 15 (68)** |

*The reaction was conducted in the presence of benzoic acid (10 mol %)
**o-xylene (boiling point 144° C.) was used as the solvent
†dichloroethane (boiling point 83° C.) was used as the solvent

TABLE 8

$$R-\underset{OH}{\underset{|}{CH}}-COOH + HN(R')(R'') \xrightarrow[\text{toluene (5 mL)}]{\text{MeB(OH)}_2 \text{ (X mol \%)}}_{\text{azeotropic reflux}} R-\underset{OH}{\underset{|}{CH}}-C(O)-N(R')(R'')$$

1.25 mmol    1.25 mmol

| Experimental example | Carboxylic acid | Amine | Amount of catalyst (mol %) | Time (h) | Yield (%) |
|---|---|---|---|---|---|
| 76 | CH$_3$(CH$_2$)$_5$CH(OH)COOH | H$_2$N-CH$_2$Ph | 1 | 12 | 91 |
| 77 |  | H$_2$N-CH$_2$CH$_2$Ph | 1 | 8 | 91 |
| 78 |  | H$_2$N-CH(Ph)$_2$ | 1 | 8 | 96 |
| 79 |  | HN(Me)CH$_2$Ph | 1 | 12 | 89 |
| 80 | (CH$_3$)$_2$C(OH)COOH | H$_2$N-CH$_2$Ph | 1 | 12 | 93 |
| 81 |  | H$_2$N-CH$_2$CH$_2$Ph | 1 | 17 | 86 |
| 82 |  | H$_2$N-CH(Ph)$_2$ | 1 | 17 | 78 |

Experimental Examples 83 and 84

The amide condensation involving salicylic acid that was a β-hydroxycarboxylic acid was performed in the presence of methylboronic acid catalyst. The synthesis procedures were similar to those in Experimental example 59. The results are described in Table 9. When xylene (boiling point 144° C.) was used as the reaction solvent, the reaction was allowed to proceed favorably (Experimental example 83). In contrast, the reactivity was low when the reaction was conducted in the absence of the methylboronic acid catalyst (Experimental example 84). Experimental example 83 corresponds to Inventive Example.

TABLE 9

| Experimental example | Catalyst | Solvent | Time (h) | Yield (%) |
|---|---|---|---|---|
| 83 | MeB(OH)$_2$ (10 mol %) | o-xylene | 14 | 99 |
| 84 | — | o-xylene | 14 | 7 |

The present application claims priority from Japanese Patent Application No. 2012-32400 filed on Feb. 17, 2012, the entire contents of which are incorporated in the present specification by reference.

INDUSTRIAL APPLICABILITY

The present invention is useful mainly in the drug and chemical industries. For example, the invention may be used in the manufacturing of such products as drug medicines, agricultural chemicals and cosmetic intermediates.

The invention claimed is:

1. A method for production of hydroxycarboxylic acid amide compounds, comprising performing amide condensation between an α- or β-hydroxycarboxylic acid compound and an amine compound in the presence as a catalyst of an alkylboronic acid represented by $R^3B(OH)_2$ (wherein $R^3$ is a primary alkyl group) or performing amide condensation between an α-hydroxycarboxylic acid compound and an amine compound in the presence as a catalyst of an arylboronic acid compound to produce a hydroxycarboxylic acid amide compound, the arylboronic acid compound being represented by Formula (1):

[Chem. 1]

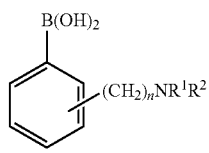

(1)

(in Formula (1), —(CH$_2$)$_n$NR$^1$R$^2$ is bonded at an ortho position or a para position, n is 1, and —NR$^1$R$^2$ is a 2,2,6,6-tetraalkylpiperidinyl).

2. The method for production of hydroxycarboxylic acid amide compounds according to claim 1, wherein in Formula (1), —(CH$_2$)$_n$NR$^1$R$^2$ is bonded at the ortho position and —NR$^1$R$^2$ is a 2,2,6,6-tetramethylpiperidinyl.

3. The method for production of hydroxycarboxylic acid amide compounds according to claim 1, wherein the amine compound is a secondary amine or an aromatic amine.

4. The method for production of hydroxycarboxylic acid amide compounds according to claim 1, wherein the amide condensation is performed under weakly acidic conditions.

5. The method for production of hydroxycarboxylic acid amide compounds according to claim 1, wherein the hydroxycarboxylic acid compound is added in excess over the amine compound or the reaction is performed in the presence of a carboxylic acid compound having lower reactivity than the hydroxycarboxylic acid compound.

6. The method for production of hydroxycarboxylic acid amide compounds according to claim 1, wherein the amide condensation is performed in a reaction solvent while performing azeotropic dehydration.

7. The method for production of hydroxycarboxylic acid amide compounds according to claim 1, wherein the amide condensation is performed in a hydrocarbon solvent containing water while performing azeotropic dehydration.

* * * * *